US010329605B2

(12) United States Patent
Albitar

(10) Patent No.: US 10,329,605 B2
(45) Date of Patent: Jun. 25, 2019

(54) METHOD TO INCREASE SENSITIVITY OF DETECTION OF LOW-OCCURRENCE MUTATIONS

(71) Applicant: NEOGENOMICS LABORATORIES, INC., Fort Myers, FL (US)

(72) Inventor: Maher Albitar, Valley Center, CA (US)

(73) Assignee: NEOGENOMICS LABORATORIES, INC., Fort Myers, FL (US)

(*) Notice: Subject to any disclaimer, the term of this patent is extended or adjusted under 35 U.S.C. 154(b) by 306 days.

(21) Appl. No.: 15/134,302

(22) Filed: Apr. 20, 2016

(65) Prior Publication Data

US 2016/0340725 A1    Nov. 24, 2016

Related U.S. Application Data

(60) Provisional application No. 62/150,198, filed on Apr. 20, 2015.

(51) Int. Cl.
*C12Q 1/68* (2018.01)
*C12P 19/34* (2006.01)
*C12Q 1/6858* (2018.01)
*C12Q 1/6869* (2018.01)
*C12Q 1/6886* (2018.01)

(52) U.S. Cl.
CPC ......... *C12Q 1/6858* (2013.01); *C12Q 1/6869* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 2003/0148273 | A1 | 8/2003 | Dong et al. |
| 2010/0009355 | A1 | 1/2010 | Kolodney |
| 2011/0217714 | A1 | 9/2011 | Makrigiorgos |
| 2014/0031240 | A1 | 1/2014 | Behlke et al. |
| 2014/0249142 | A1 | 9/2014 | Treon |
| 2014/0335514 | A1 | 11/2014 | Arnold |
| 2016/0194691 | A1* | 7/2016 | Powell ................. C12Q 1/6858 506/2 |

FOREIGN PATENT DOCUMENTS

| | | |
|---|---|---|
| WO | 1996017945 A1 | 6/1996 |
| WO | 2013123031 A2 | 8/2013 |
| WO | 2015085075 A1 | 6/2015 |

OTHER PUBLICATIONS

Siebolts et al., "Establishment of a Highly Sensitive Allele Specific Wild Type Blocker Polymerase Chain Reaction Followed by Pyrosequencing for Detection of the p.D816V Point Mutation," Blood, vol. 114, pp. 1-4. (Year: 2009).*

Knierim et al., "Systemic Comparison of Three Methods for Fragmentation of Long-Range PCR Products for Next Generation Sequencing," PLoS ONE, vol. 6, No. 11, e28240, pp. 1-6. (Year: 2011).*
Sikkema-Raddatz et al., "Targeted Next-Generation Sequencing can Replace Sanger Sequencing in Clinical Diagnostics," Human Mutations, vol. 34, No. 7, pp. 1035-1042. (Year: 2013).*
Efrati et al., "LNA-based PCR clamping enrichment assay for the identification of KRAS mutations," Cancer Biomarkers, vol. 8, pp. 89-94. (Year: 2010).*
"An Introduction to Next-Generation Sequencing Technology", Illumina, Inc., 2011-2013, 12 pages.
Adams, RL, et al., "CpG deficiency, dinucleotide distributions and nucleosome positioning," Eur Biochem 1987, 165 (1): 107:115.
Adams, RLP, et al., "Increased G+C content of DNA stabilises methyl CpG dinucieotides," Nucl Acids Res 1984, 12 (14): 5869-5877.
Albitar, A. et al., "Positive Selection and High Sensitivity Test for MYD88 Mutations Using Locked Nucleic Acid," International Journal of Laboratory Hematology, Jan. 21, 2016, vol. 38, pp. 133-140.
Capaldi, IB et al, "Detection of MYD88 L265P Mutations in Formalin-Fixed and Decalcified BM Biopsies from Patients with Lymphoplasmacytic Lymphoma," Experimental and Molecular Pathology, May 16, 2014, vol. 97, pp. 57-65.
Do, H, et al., "Reducing sequence artifacts in amplicon-based massively parallel sequencing of formalin-fixed paraffin-embedded DNA by enzymatic depletion of uracil-containing templates," Clin Chem 2013, 59(9), 1376-1383.
Do, H. et al., "Dramatic Reduction of Sequence Artefacts from DNA Isolated from Formalin-Fixed Cancer Biopsies by Treatment with the Uracil-DNA Glycosylase," Oncotarget, May 24, 2012, vol. 3, pp. 546-558.
Dominguez, PL et al., Wild-Type Blocking Polymerase Chain Reaction for Detection of Single Nucleotide Minority Mutations from Clinical Specimens, Oncogene, Aug. 22, 2005, vol. 24, pp. 6830-6834.
Gallegos-Ruiz, MI, et al., "EGFR and K-ras mutation analysis in non-small cell lung cancer: comparison of paraffin embedded versus frozen specimens," Cell Oncol 2007, 29(3): 257-264.
GenBank NM_033360.3—*Homo sapiens* Kirsten rat sarcoma viral oncogene homolog (KRAS), transcript variant a, mRNA [online] Mar. 15, 2015, retrieved Sep. 12, 2016, available at <URL :http://www.ncbi.nlm.nih.gov/nuccore/575403058?sat=21&satkey=33223617>.
Haley L., et al., "Performance characteristics of next-generation sequencing in clinical mutation detection of colorectal cancers", Mod. Pathol. Oct. 2015; 28(10): 1390-1399.

(Continued)

*Primary Examiner* — Young J Kim
(74) *Attorney, Agent, or Firm* — Eleanor Musick; Musick Davison LLP

(57) ABSTRACT

A method for detecting a low-occurrence mutation in isolated DNA adds a blocking probe to reagents during amplification of the isolated DNA. The blocking probe is an oligonucleotide complementary to wild-type DNA corresponding to the sample. The blocking probe spans a site of a suspected mutation within a region of interest in the isolated DNA. After amplification, fragments of the amplified DNA is sequenced using next generating sequencing and an output is generated to display the sequenced fragments. In some embodiments, the blocking probe is locked nucleic acid (LNA).

10 Claims, 9 Drawing Sheets

Specification includes a Sequence Listing.

(56) References Cited

OTHER PUBLICATIONS

Loiarro, M, at al., "Identification of critical residues of the MyD88 death domain involved in the recruitment of downstream kinases", J Biol Chem 2009, 284(41): 28093-28103.

Morlan et al, Mutation detection by real-time PCR: a simple, robust and highly selective method, PLosS One Feb. 25, 2009 vol. 4 No. 2, pp. e4584 1-11 and Table S1 (appended as p. 12).

Ngo, VN, et al., "Oncogenically active MYD88 mutations in human lymphoma", Nature 2011, 470(7332): 115-119.

Pasqualucci, L., et al., "Analysis of the coding genome of diffuse large B-cell lymphoma," Nat Genet 2011, 43(9): 830-837.

PCT/US2016/028517, International Search Report and Written Opinion, dated Sep. 2, 2016, 9 pages.

Salar, A., et al., 1690 MYD88 (L265P) Mutation Confers Very Poor Response and Outcome after Second-Line Therapy in Patients with Diffuse Large B-Cell Lymphoma (DLBCL), Presentation at 56th American Society of Hematology Meeting and Exposition, San Francisco, CA, 2014.

Treon, SP, et al., "MYD88 L265P somatic mutation in Waldenström's macroglobulinemia.", N Engl J Med 2012, 367(9): 826-833.

Troen, G, et al, CD79B and MYD88 Mutations in Splenic Marginal Zone Lymphoma. ISRN Oncology, 2013, 252318.

Varettoni, M, et al., "Prevalence and clinical significance of the MYD88 (L265P) somatic mutation in Waldenström's macroglobulinemia and related lymphoid neoplasms", Blood 2013, 121(13): 2522-2528.

Wang, D, et al., "508 Novel Approach to the Potential Treatment of Patients with B-Cell Lymphomas Harboring the MYD88 L265P Mutation: Combination Treatment with TLR Antagonist and Rituximab", Presentation at 56th American Society of Hematology Meeting and Exposition, San Francisco, CA, 2014.

Xu L, et al., "MYD88 L265P in Waldenström macroglobulinemia, immunoglobulin M monoclonal gammopathy, and other B-cell lymphoproliferative disorders using conventional and quantitative allele-specific polymerase chain reaction", Blood 2013, 121(11): 2051-2058.

Yost, SE, et al, "Identification of high-confidence somatic mutations in whole genome sequence of formalin-fixed breast cancer specimens," Nucleic Acids Res 2012, 40 (14).

\* cited by examiner

NTP14-001453

| Gene_0 | HGVSc_42 | HGVSp_43 | Alt Variant Freq_13 | Amino Acids_32 | Codons_33 | Read Depth_14 | Consequence_28 | Sift_39 |
|---|---|---|---|---|---|---|---|---|
| APC | NM_000038.5: c.4014_4015delGG | NP_000029.2: p.Gly1339PhefsTer2 | 8.97 | | | 9878 | frameshift_variant, feature_truncation | |
| KRAS | NM_033360.2: c.35G>T | NP_203524.1: p.Gly12Val | 6.04 | G/V | gGt/gTt | 9207 | missense_variant | deleterious(0) |
| TP53 | NM_000546.5: c.572_574delCTC | NP_000537.3: p.Pro191del | 7.92 | P/Q | cCTCag/cag | 5633 | inframe_deletion | |

NTP14-1453-With Selection

| Gene_0 | HGVSc_43 | HGVSp_44 | Alt Variant Freq_13 | Amino Acids_33 | Codons_34 | Read Depth_14 | Consequence_29 | Sift_40 |
|---|---|---|---|---|---|---|---|---|
| APC | NM_000038.5: c.4014_4015delGG | NP_000029.2: p.Gly1339PhefsTer2 | 13.37 | | | 7143 | frameshift_variant, feature_truncation | |
| KRAS | NM_033360.2: c.35G>T | NP_203524.1: p.Gly12Val | 97.96 | G/V | gGt/gTt | 393 | missense_variant | deleterious(0) |
| TP53 | NM_000546.5: c.572_574delCTC | NP_000537.3: p.Pro191del | 12.1 | P/Q | cCTCag/cag | 7547 | inframe_deletion | |

FIG. 3

NTP14-001685

| Gene_0 | HGVSc_43 | HGVSp_44 | Alt Variant Freq_13 | Amino Acids_33 | Read Depth_14 | Codons_34 | Consequence_29 | Sift_40 |
|---|---|---|---|---|---|---|---|---|
| EGFR | NM_005228.3: c.2235_2249del GGAATTAAGAGAAGC (SEQ ID NO. 5) | NP_005219.2: p.Glu746_Ala750del | 36.6 | KELREA/K | 52195 | aaGGAATTAAGAGAAGCa/aaa | missense_variant, feature_truncation | |
| EGFR, EGFR-AS1 | NM_005228.3: c.2369C>T | NP_005219.2: p.Thr790Met | 19.2 | T/M | 12909 | aCg/aTg | missense_variant | deleterious(0) |
| TP53 | NM_000546.5: c.527G>T | NP_000537.3: p.Cys176Phe | 10.95 | C/F | 22898 | tGc/tTc | missense_variant | deleterious(0) |

NTP14-001685-With Selection

| Gene_0 | HGVSc_43 | HGVSp_44 | Alt Variant Freq_13 | Amino Acids_33 | Read Depth_14 | Codons_34 | Consequence_29 | Sift_40 |
|---|---|---|---|---|---|---|---|---|
| EGFR | NM_005228.3: c.2235_2249del GGAATTAAGAGAAGC | NP_005219.2: p.Glu746_Ala750del | 38.61 | KELREA/K | 61154 | aaGGAATTAAGAGAAGCa/aaa | missense_variant, feature_truncation | |
| EGFR, EGFR-AS1 | NM_005228.3: c.2369C>T | NP_005219.2: p.Thr790Met | 94.42 | T/M | 6380 | aCg/aTg | missense_variant | deleterious(0) |
| TP53 | NM_000546.5: c.527G>T | NP_000537.3: p.Cys176Phe | 16.45 | C/F | 26295 | tGc/tTc | missense_variant | deleterious(0) |

FIG. 4

| Case No. | Exon | EGFR NGS-TSACP panel added T790LNA | | ave read/unif.% |
|---|---|---|---|---|
| | | EGFR-T790LNA | EGFR44.chr755249005 (cover T790M) reads | |
| MOL15-001572 | ex20 | T790M, (96.5%) | 8770 | 42432/88.4% |
| MOL15-001733 | ex21 | L858R (27.6%), | 40 | 37773/81.8% |
| MOL15-001792 | ex19 | E7546_A750 del, (24.9%) | 171 | 37691/88.9% |
| MOL15-001877 | ex19/ex20 | E746_A750 del (63.9%), **T790S fs*36(7.96%)** | 164 | 37827/86.2% |
| MOL15-002073 | ex19 | E746_T751 del/insA, 12.9% | 83 | 38099/90.7% |
| MOL15-002080 | ex18 | G719A, 62.6% | 93 | 35727/86.2% |
| MOL15-000010 | ex19 | L747S + A750_K754 del | 327 | 17997/86.2% |
| MOL15-000244 | ex19 | EGFR gene amplification, L747_P753delinsS, 95% | 5382* | 33430/80% |
| MOL15-000398 | ex18/ex20 | G719A(16.5%), S768I (10.3%) | 231 | 41224/85.8% |

| ABL1 | BRAF | CHEK1 | FANCC | GATA3 | JAK2 | MITF | PDCD1LG2 | RBM10 | STAT4 |
|---|---|---|---|---|---|---|---|---|---|
| ABL2 | BRCA1 | CHEK2 | FANCD2 | GATA4 | JAK3 | MLH1 | PDGFRA | RET | STK11 |
| ACVR1B | BRCA2 | CIC | FANCE | GATA6 | JUN | MPL | PDGFRB | RICTOR | SUFU |
| AKT1 | BRD4 | CREBBP | FANCF | GID4 | KAT6A | MRE11A | PDK1 | RNF43 | SYK |
| AKT2 | BRIP1 | CRKL | FANCG | GLI1 | KDM5A | MSH2 | PIK3C2B | ROS1 | TAF1 |
| AKT3 | BTG1 | CRLF2 | FANCL | GNA11 | KDM5C | MSH6 | PIK3CA | RPTOR | TBX3 |
| ALK | BTK | CSF1R | FAS | GNA13 | KDM6A | MTOR | PIK3CB | RUNX1 | TERC |
| AMER1 | C11orf30 | CTCF | FAT1 | GNAQ | KDR | MUTYH | PIK3CG | RUNX1T1 | TERT |
| APC | CARD11 | CTNNA1 | FBXW7 | GNAS | KEAP1 | MYC | PIK3R1 | SDHA | TET2 |
| AR | CBFB | CTNNB1 | FGF10 | GPR124 | KEL | MYCL | PIK3R2 | SDHB | TGFBR2 |
| ARAF | CBL | CUL3 | FGF14 | GRIN2A | KIT | MYCN | PLCG2 | SDHC | TNFAIP3 |
| ARFRP1 | CCND1 | CYLD | FGF19 | GRM3 | KLHL6 | MYD88 | PMS2 | SDHD | TNFRSF14 |
| ARID1A | CCND2 | DAXX | FGF23 | GSK3B | KMT2A | NF1 | POLD1 | SETD2 | TOP1 |
| ARID1B | CCND3 | DDR2 | FGF3 | H3F3A | KMT2C | NF2 | POLE | SF3B1 | TOP2A |
| ARID2 | CCNE1 | DICER1 | FGF4 | HGF | KMT2D | NFE2L2 | PPP2R1A | SLIT2 | TP53 |
| ASXL1 | CD274 | DNMT3A | FGF6 | HNF1A | KRAS | NFKBIA | PRDM1 | SMAD2 | TSC1 |
| ATM | CD79A | DOT1L | FGFR1 | HRAS | LMO1 | NKX2-1 | PREX2 | SMAD3 | TSC2 |
| ATR | CD79B | EGFR | FGFR2 | HSD3B1 | LRP1B | NOTCH1 | PRKAR1A | SMAD4 | TSHR |
| ATRX | CDC73 | EP300 | FGFR3 | HSP90AA1 | LYN | NOTCH2 | PRKCI | SMARCA4 | U2AF1 |
| AURKA | CDH1 | EPHA3 | FGFR4 | IDH1 | LZTR1 | NOTCH3 | PRKDC | SMARCB1 | VEGFA |
| AURKB | CDK12 | EPHA5 | FH | IDH2 | MAGI2 | NPM1 | PRSS8 | SMO | VHL |
| AXIN1 | CDK4 | EPHA7 | FLCN | IGF1R | MAP2K1 | NRAS | PTCH1 | SNCAIP | WISP3 |
| AXL | CDK6 | EPHB1 | FLT1 | IGF2 | MAP2K2 | NSD1 | PTEN | SOCS1 | WT1 |
| BAP1 | CDK8 | ERBB2 | FLT3 | IKBKE | MAP2K4 | NTRK1 | PTPN11 | SOX10 | XPO1 |
| BARD1 | CDKN1A | ERBB3 | FLT4 | IKZF1 | MAP3K1 | NTRK2 | QKI | SOX2 | ZBTB2 |
| BCL2 | CDKN1B | ERBB4 | FOXL2 | IL7R | MCL1 | NTRK3 | RAC1 | SOX9 | ZNF217 |
| BCL2L1 | CDKN2A | ERG | FOXP1 | INHBA | MDM2 | NUP93 | RAD50 | SPEN | ZNF703 |
| BCL2L2 | CDKN2B | ERRFI1 | FRS2 | INPP4B | MDM4 | PAK3 | RAD51 | SPOP | |
| BCL6 | CDKN2C | ESR1 | FUBP1 | IRF2 | MED12 | PALB2 | RAF1 | SPTA1 | |
| BCOR | CEBPA | EZH2 | GABRA6 | IRF4 | MEF2B | PARK2 | RANBP2 | SRC | |
| BCORL1 | CHD2 | FAM46C | GATA1 | IRS2 | MEN1 | PAX5 | RARA | STAG2 | |
| BLM | CHD4 | FANCA | GATA2 | JAK1 | MET | PBRM1 | RB1 | STAT3 | |

METHOD TO INCREASE SENSITIVITY OF DETECTION OF LOW-OCCURRENCE MUTATIONS

RELATED APPLICATIONS

This application claims the benefit of the priority of U.S. Provisional Application No. 62/150,198, filed Apr. 20, 2015, which is incorporated herein by reference.

SEQUENCE LISTING

This application includes a sequence listing submitted as a text file via the U.S. Patent and Trademark Office's Electronic Filing System, which sequence listing is incorporated herein by reference.

FIELD OF THE INVENTION

The present invention relates to a method for enhancing the sensitivity of next generation sequencing of low-occurrence mutations and more particularly to a method for selectively blocking portions of the fragments from amplification prior to NGS.

BACKGROUND OF THE INVENTION

Since the introduction of next-generation sequencing (NGS) technology, there has been a major transformation in the way researchers extract genetic information from biological systems, opening the way to expanded insight about the genome, transcriptome, and epigenome of any species. This ability has catalyzed a number of important breakthroughs, advancing fields from human disease research to agriculture and evolutionary science.

In principle, the concept behind NGS technology is similar to capillary electrophoresis (CE)-based Sanger sequencing: the bases of a small fragment of DNA are sequentially identified from signals emitted as each fragment is re-synthesized from a DNA template strand. (See, e.g., Metzker, M., *Nature Biotechnology Reviews* (2010) 11:31-46, which is incorporated herein by reference.) NGS extends this process across millions of reactions in a massively parallel fashion, without being limited to a single or a few DNA fragments. This advance enables rapid sequencing of large strings of DNA base pairs spanning entire genomes, with the latest instruments being capable of producing hundreds of gigabases of data in a single sequencing run. NGS differs from conventional Sanger sequencing in that in conventional Sanger sequencing, all copies of the DNA are sequenced together, while in NGS, the DNA is separated into small fragments that are isolated and individually sequenced. This distinction has implications in terms of procedures to enhance the sensitivity of the procedure for low-occurrence mutation detection.

With the advent of NGS, sequencing and testing for mutations has become a standard procedure in the diagnosis and management of patients with cancer. Screening for various mutations in cancer tissue provides a means for predicting prognosis and for determining therapy. Precision medicine and targeted therapy depends on the detection of molecular abnormalities and selecting therapy that target these molecular abnormalities. For example, the detection of EGFR mutation in a patient with cancer indicates that this patient most likely will respond to anti-EGFR kinase inhibitors. On the other hand, the detection of certain mutations may imply resistance to specific therapy. For example, the detection of the EGFR T790M mutation in a patient with cancer indicates that this patient will not respond to EGFR therapy.

Detection of mutations in specific genes is most commonly achieved using targeted tests that are designed to detect one or at least a small number of mutations in a single gene. NGS is gaining momentum as a complementary test for a number of reasons. Firstly, clinical trials for targeted cancer therapies rely on detection of mutations that are frequently not covered by existing targeted tests. Instead of relying on the slow and labor-intensive process of validating and implementing a new molecular assay to test for one or a few mutations, NGS simplifies the task of providing coverage of one or more additional mutations of interest. Second, targeted tests can provide misleading results, failing to identify therapeutically-targetable mutations. Further, targeted tests may fail to detect the very mutation they are designed to detect. Finally, tumors frequently harbor mutations that are therapeutically-targetable but are not typically seen in that tumor type. Due to its massively parallel nature, NGS is well suited for detecting mutations in unexpected genes.

Other technologies that have typically been used to measure minimal residual disease, like Sanger sequencing, cannot reliably detect mutations below 10 percent to 20 percent frequency. Experts agree that mutations present below 10 percent frequency are clinically significant, however, the appropriate threshold for defining a "significant" mutation requiring intervention has not yet been established. While NGS has provided a valuable tool for detecting mutations with a sensitivity in the range of 5 percent, it remains less sensitive for the detection of mutations that present in less than 5 percent of the analyzed DNA. This particularly becomes a problem when attempting to analyze peripheral blood plasma or other body fluids such as urine or bronchial lavage. Accordingly, the need remains for method for improving the sensitivity of NGS for purposes of detecting low-occurrence mutations.

BRIEF SUMMARY

In one aspect of the invention, a method is provided for enriching for the mutant DNA and reducing the relative ratio of the wild-type DNA in the analyzed sample through selective sequencing. In an exemplary embodiment, a locked nucleic acid (LNA) probe that is identical to the wild-type is used to block the wild type DNA amplification while the mutant DNA is enriched for sequencing using amplicon-based NGS procedure. LNA probe is structurally different from normal DNA and when it binds to DNA, the binding is very strong and disassociating it for amplification becomes very difficult even at high temperature, thus preventing amplification.

In other embodiments, selective sequencing can be achieved using techniques including ICE COLD-PCR (Improved & Complete Enrichment Co-amplification at Lower Denaturation temperature), which preferentially enriches mutant DNA sequences in an excess of wild-type DNA using an oligonucleotide complementary to wild-type sequence (RS-oligo). ICE COLD-PCR has been reported to significantly improve sensitivity in standard Sanger sequencing analysis. Another approach is the QClamp™ technology (from DiaCarta), which is used to screen for somatic mutations by utilizing a sequence specific wild-type template xeno-nucleic acid "Clamp" (XNA) that suppresses PCR amplification of wild-type template DNA and allows selective PCR amplification of only mutant templates. This allows the detection of mutant DNA in the presence of a large excess of wild-type template.

In one aspect of the invention, a method of detecting a low-occurrence mutation in a sample from a patient includes: isolating DNA from the sample; adding a blocking probe to the isolated DNA, the blocking probe comprising an oligonucleotide complementary to wild-type DNA corresponding to the sample, the blocking probe adapted to span a site of a suspected mutation within a region of interest in the isolated DNA; amplifying the isolated DNA; sequencing fragments of the amplified DNA using next generating sequencing; and generating an output corresponding to the sequenced fragments. In some embodiments, the blocking probe is locked nucleic acid (LNA); in other embodiments, the blocking probe is selected from block nucleic acid (BNA), QClamp and ICE COLD-PCR. The blocking probe may be a 10mer to 12mer. In embodiments where the region of interest is KRAS codon 12, the blocking probe is CCTACGCCACAGCTCCAA (SEQ ID NO. 1). In embodiments in which the region of interest is EGFR codon T790, the blocking probe is CTCATCACGCAGCTC (SEQ ID NO. 2).

In certain embodiments, prior to adding a blocking probe, the isolated DNA is fragmented into fragments comprising one or more regions of interest. In other embodiments, prior to amplifying the isolated DNA, the isolated DNA is hybridized with one or more enrichment probes to tag and fragment the DNA. The sample may be selected from the group consisting of whole blood, stool, biopsied tissue, bone marrow, fine needle aspirate (FNA), and peripheral blood.

In another aspect of the invention, a method for detecting a low-occurrence mutation in isolated DNA includes: adding a blocking probe to reagents during amplification of the isolated DNA, wherein the blocking probe comprises an oligonucleotide complementary to wild-type DNA corresponding to the sample, the blocking probe adapted to span a site of a suspected mutation within a region of interest in the isolated DNA; sequencing fragments of the amplified DNA using next generating sequencing; and generating an output corresponding to the sequenced fragments. In some embodiments, the blocking probe is locked nucleic acid (LNA); in other embodiments, the blocking probe is selected from block nucleic acid (BNA), QClamp and ICE COLD-PCR. The blocking probe may be a 10mer to 12mer. In embodiments where the region of interest is KRAS codon 12, the blocking probe is CCTACGCCACAGCTCCAA (SEQ ID NO. 1). In embodiments in which the region of interest is EGFR codon T790, the blocking probe is CTCATCACGCAGCTC (SEQ ID NO. 2).

In certain embodiments, prior to adding a blocking probe, the isolated DNA is fragmented into fragments comprising one or more regions of interest. In other embodiments, prior to amplifying the isolated DNA, the isolated DNA is hybridized with one or more enrichment probes to tag and fragment the DNA. The sample may be selected from the group consisting of whole blood, stool, biopsied tissue, bone marrow, fine needle aspirate (FNA), and peripheral blood.

BRIEF DESCRIPTION OF THE DRAWINGS

FIG. 3 is a table comparing NGS results obtained with and without LNA for the detection of KRAS mutation.

FIG. 4 is a table comparing NGS results obtained with and without LNA for the detection of EGFR mutation.

FIG. 6 is a table showing results of NGS sequencing for detecting EGFR mutation with enhanced methods according to an embodiment of the invention.

FIG. 7 is a table listing genes in a custom-designed 315 panel for hybrid capture NGS.

DETAILED DESCRIPTION OF EXEMPLARY EMBODIMENTS

Figure 1A:
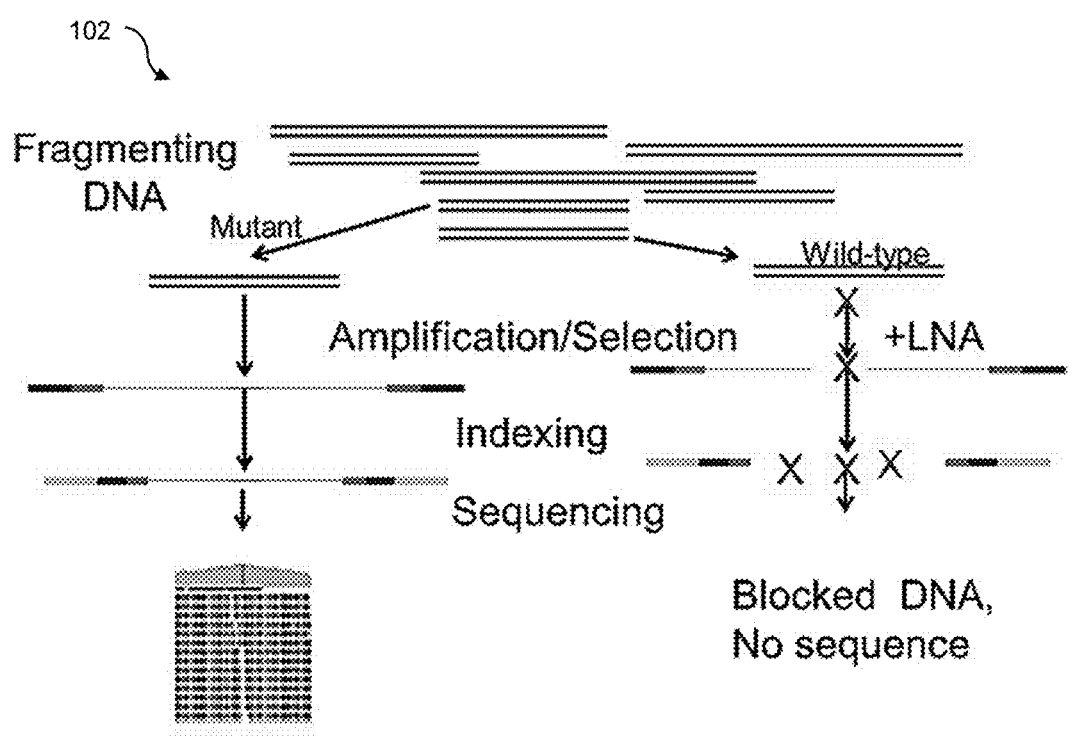
FIG. 1A is a diagram showing the use of LNA for selecting mutant DNA for amplicon-based NGS according to an embodiment of the invention.

The following written description and accompanying drawings identify certain gene names, accession numbers, and other identifiers that will be readily recognized by those of skill in the art as referring to information that is available via the National Center for Biotechnology Information (NCBI) public databases. Additional information contained in the NCBI databases corresponding to any identified genes, fragments, probes, amino acids, and accession numbers, including sequence listings, is incorporated herein by reference.

The inventive method improves sensitivity of NGS analysis by enriching for the mutant DNA and reducing the relative ratio of the wild-type DNA in the analyzed sample through selective sequencing. In an exemplary embodiment, a locked nucleic acid (LNA) probe that is identical to the wild-type is used to block the wild type DNA amplification while the mutant DNA is enriched for sequencing using amplicon-based NGS procedure. A LNA is structurally different from normal DNA and when it binds to DNA, the binding is very strong such that disassociating it for amplification becomes very difficult, even at high temperature, thus preventing amplification.

Locked nucleic acids (LNAs) are a nucleic acid analog that may be used for increasing oligonucleotide hybridization strength and specificity. The LNA bases can be incorporated into any DNA or RNA oligonucleotide and induce a conformational change in the local helix. This altered state provides the LNA bases with stronger binding strength for complementary sequences, greater mismatch discrimination, and enhanced duplex formation. These features increase amplification success when LNAs are incorporated into oligonucleotides and also increase duplex melting temperatures, which enable probes and primers to be shortened and give greater specificity. Applications for LNAs to date include allele-specific PCR, TaqMan and Molecular Beacon probes, real-time PCR probes, antisense oligonucleotides, microarray probes, and PCR primers.

The incorporation of LNA nucleotides into real-time PCR probes and primers decreases $C_t$ values significantly, with a corresponding increase in amplification efficiency. For standard PCR, LNA modifications increase the specificity of the amplification, resulting in improved sequencing read quality, and can reduce the amount of template required by at least 10-fold. For many applications, the ability to detect these lower amounts, even as little as one or two copies of a target sequence, would be highly desirable.

As used herein, the term "gene" means a nucleic acid sequence that is transcribed (DNA) to RNA in vitro or in vivo when operably linked to appropriate regulatory sequences. The gene can include regulatory regions preceding and following the coding region, e.g. 5' untranslated (5'UTR) or "leader" sequences and 3' UTR or "trailer" sequences, as well as intervening sequences (introns) between individual coding segments (exons).

As used herein, the term "nucleic acid" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA. A "portion" of a nucleic acid molecule refers to contiguous set of nucleotides comprised by that molecule. A portion can comprise all or only a subset of the nucleotides comprised by the molecule. A portion can be double-stranded or single-stranded.

Nucleic acids (e.g., DNA or RNA) may be isolated from a biological sample containing a variety of other components, such as proteins, lipids, and other (e.g., non-target or non-template) nucleic acids. Nucleic acid molecules can be obtained from any material (e.g., cellular material (live or dead), extracellular material, viral material, environmental samples (e.g., metagenomic samples), synthetic material (e.g., amplicons such as provided by PCR or other amplification technologies)), obtained from an animal, plant, bacterium, archaeon, fungus, or any other organism. Biological samples for use in the present technology include viral particles or preparations thereof. In some embodiments a nucleic acid is isolated from a sample for use as a template in an amplification reaction (e.g., to prepare an amplicon library or fragment library for sequencing). In some embodiments a nucleic acid is isolated from a sample for use in preparing a library of fragments.

Nucleic acid molecules can be obtained directly from an organism or from a biological sample obtained from an organism, e.g., from blood, urine, cerebrospinal fluid, seminal fluid, saliva, sputum, stool, hair, sweat, tears, skin, and tissue.

Exemplary samples include, but are not limited to, whole blood, lymphatic fluid, serum, plasma, buccal cells, sweat, tears, saliva, sputum, hair, skin, biopsy, cerebrospinal fluid (CSF), amniotic fluid, seminal fluid, vaginal excretions, serous fluid, synovial fluid, pericardial fluid, peritoneal fluid, pleural fluid, transudates, exudates, cystic fluid, bile, urine, gastric fluids, intestinal fluids, fecal samples, and swabs, aspirates (e.g., bone marrow, fine needle, etc.), washes (e.g., oral, nasopharyngeal, bronchial, bronchialalveolar, optic, rectal, intestinal, vaginal, epidermal, etc.), and/or other specimens.

Any tissue or body fluid specimen may be used as a source for nucleic acid for use in the technology, including forensic specimens, archived specimens, preserved specimens, and/or specimens stored for long periods of time, e.g., fresh-frozen, methanol/acetic acid fixed, or formalin-fixed paraffin embedded (FFPE) specimens and samples. Nucleic acid template molecules can also be isolated from cultured cells, such as a primary cell culture or a cell line. The cells or tissues from which template nucleic acids are obtained can be infected with a virus or other intracellular pathogen.

A sample can also be total RNA extracted from a biological specimen, a cDNA library, viral, or genomic DNA. A sample may also be isolated DNA from a non-cellular origin, e.g. amplified/isolated DNA that has been stored in a freezer.

Nucleic acid molecules can be obtained, e.g., by extraction from a biological sample, e.g., by a variety of techniques such as those described by Maniatis, et al. (1982) Molecular Cloning: A Laboratory Manual, Cold Spring Harbor, N.Y. (see, e.g., pp. 280-281).

In various embodiments, a nucleic acid is amplified. Any amplification method known in the art may be used. Examples of amplification techniques that can be used include, but are not limited to, PCR, quantitative PCR, quantitative fluorescent PCR (QF-PCR), multiplex fluorescent PCR (MF-PCR), real time PCR (RT-PCR), single cell PCR, restriction fragment length polymorphism PCR (PCR-RFLP), hot start PCR, nested PCR, in situ polony PCR, in situ rolling circle amplification (RCA), bridge PCR, picotiter PCR, and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR), and nucleic acid based sequence amplification (NABSA). Other amplification methods that can be used herein include those described in U.S. Pat. Nos. 5,242,794; 5,494,810; 4,988,617; and 6,582,938.

The term "isolated" or "partially purified" as used herein refers, in the case of a nucleic acid, to a nucleic acid separated from at least one other component (e.g., nucleic acid or polypeptide) that is present with the nucleic acid as found in its natural source and/or that would be present with the nucleic acid when expressed by a cell. A chemically synthesized nucleic acid or one synthesized using in vitro transcription/translation is considered "isolated."

The term "single nucleotide polymorphism" or "SNP" refers to single point variations in genomic DNA or tumor-associated DNA. The terms "mutation" and "point mutation" are meant to include and/or refer to SNPs.

As used herein, a "disease associated with a genetic alteration" refers to any disease that is caused by, at least in part, by an alteration in the genetic material of the subject as compared to a healthy wildtype subject, e.g. a deletion, an insertion, a SNP, a gene rearrangement. A disease can be caused by, at least in part, an alteration in the genetic material of the subject if the alteration increases the risk of the subject developing the disease, increases the subject's susceptibility to a disease (including infectious diseases, or diseases with an infectious component), causes the production of a disease-associated molecule, or causes cells to become diseased or abnormal (e.g. loss of cell cycle regulation in cancer cells). Diseases can be associated with multiple genetic alterations, e.g. cancers.

As used herein, the term "complementary" refers to the ability of nucleotides to form hydrogen-bonded base pairs. In some embodiment, complementary refers to hydrogen-bonded base pair formation preferences between the nucleotide bases G, A, T, C and U, such that when two given polynucleotides or polynucleotide sequences anneal to each other, A pairs with T and G pairs with C in DNA, and G pairs with C and A pairs with U in RNA.

As used herein, "specific" when used in the context of a primer specific for a target nucleic acid refers to a level of complementarity between the primer and the target such that there exists an annealing temperature at which the primer will anneal to and mediate amplification of the target nucleic acid and will not anneal to or mediate amplification of non-target sequences present in a sample.

As used herein, "amplified product", "amplification product", or "amplicon" refers to oligonucleotides resulting from an amplification reaction that are copies of a portion of a particular target nucleic acid template strand and/or its complementary sequence, which correspond in nucleotide sequence to the template nucleic acid sequence and/or its complementary sequence. An amplification product can further comprise sequence specific to the primers and which flanks sequence which is a portion of the target nucleic acid and/or its complement.

An amplicon panel is a collection of amplicons that are related, e.g., to a disease, disease progression, developmental defect, constitutional disease, metabolic pathway, pharmacogenomic characterization, trait, organism (e.g., for species identification), group of organisms, geographic location, organ, tissue, sample, environment (e.g., for metagenomic and/or ribosomal RNA), gene, chromosome, etc. For example, a cancer panel comprises specific genes or mutations in genes that have established relevancy to a particular cancer phenotype. Some amplicon panels are directed toward particular "cancer hotspots", that is, regions of the genome containing known mutations that correlate with cancer progression and therapeutic resistance.

Production of an amplicon panel is often associated with downstream next-generation sequencing to obtain the sequences of the amplicons of the panel. The amplification is used to target the genome and provide selected regions of interest (ROIs) for NGS. This target enrichment focuses sequencing efforts to specific regions of a genome.

As used herein, "blocking oligonucleotide" (also "blocking probe")" is a single stranded nucleic acid sequence, which may be one of single stranded DNA, RNA, peptide nucleic, or locked nucleic acid. The blocking oligonucleotide can be naturally- or non-naturally-occurring and generally comprises from 10 to 40 nucleotides, more preferably from 10 to 12 nucleotides. A blocking oligonucleotide is configured to modify the binding interaction (for example, melting temperature (Tm)) within a complementary target region (ROI).

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Except where otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); and Davis et al., Basic Methods in Molecular Biology, Elsevier Science Publishing, Inc., New York, USA (1995) which are all incorporated by reference herein in their entireties.

Next-generation sequencing (NGS) methods share the common feature of massively parallel, high-throughput strategies. NGS methods can be broadly divided into those that require template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., and Pacific Biosciences, respectively.

Figure 1B:
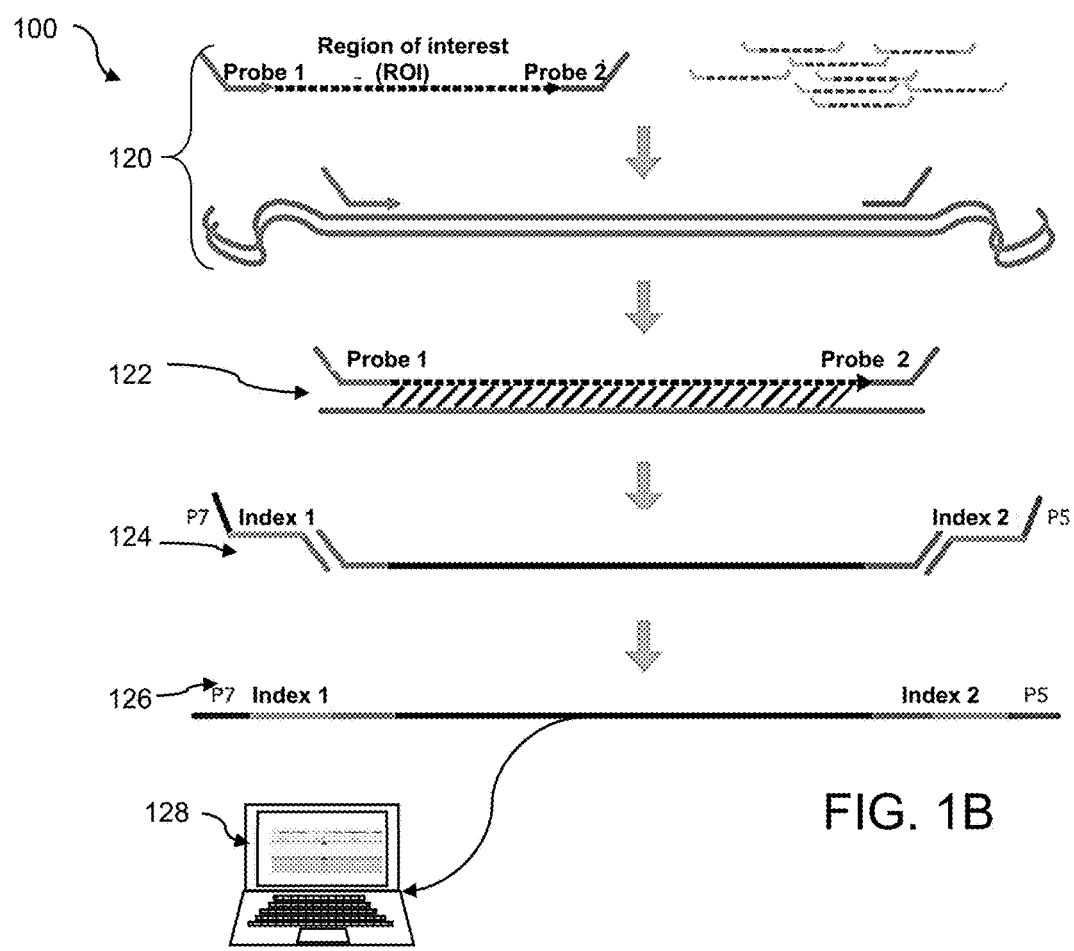
FIG. 1B is a diagram showing the basic process for amplicon-based NGC.

FIG. 1A diagrammatically illustrates the process of using LNA for selecting mutant DNA for amplicon-based NGS. FIG. 1B is a block diagram showing the process for hybrid capture-based NGS using WT-blocking to increase sensitivity for mutant DNA.

In other embodiments, selective sequencing according to the can be achieved using techniques including ICE COLD-PCR (Improved & Complete Enrichment Co-amplification at Lower Denaturation temperature), which preferentially enriches mutant DNA sequences in an excess of wild-type DNA using an oligonucleotide complementary to wild-type sequence (RS-oligo). ICE COLD-PCR has been reported to significantly improve sensitivity in standard Sanger sequencing analysis.

Another approach is the QClamp™ technology (from DiaCarta), which is used to screen for somatic mutations by utilizing a sequence specific wild-type template xenonucleic acid "Clamp" (XNA) that suppresses PCR amplification of wild-type template DNA and allows selective PCR amplification of only mutant templates. This allows the detection of mutant DNA in the presence of a large excess of wild-type template.

The following examples describe testing of the inventive method for specific mutation detection:

EXAMPLE 1

Enhancing Sensitivity of NGS in Detecting KRAS Mutation

Mutations in codon 12 and 13 of the KRAS gene are found in ~30% of colorectal cancer (CRC) cases and are associated with an increased risk of recurrence and mortality. Various preclinical and clinical studies have revealed that the presence of KRAS activating mutations in CRC correlates with resistance to EGFR monoclonal antibodies (EGFR mAb), such as cetuximab (Erbitax) and panitumumab (Vectibix). As such, the US Food and Drug Administration (FDA) has recommended that EGFR mAbs should not be given to patients with tumors harboring KRAS mutations in codon 12 or 13. This requires the KRAS mutation status to be assessed prior to treatment, yet clinicians currently lack the ability to detect these mutations with a high sensitivity, high-throughput and simple method.

Sanger sequencing is the gold standard for detecting KRAS mutations, however, it is highly inefficient and has relatively low sensitivity. In response to increasing demands in the medical setting, various KRAS mutation detection assays have been developed and described in the literature and different providers offer commercial test kits (see, e.g., Cavallini A, et al.: "KRAS genotyping as biomarker in colorectal cancer: A comparison of three commercial kits on histologic material", *Anticancer Res.* 30:5251-5256. 2010; Malapelle U, et al.: "KRAS testing in metastatic colorectal carcinoma: Challenges, controversies, breakthroughs and beyond", *J Clin Pathol.* 67:1-9. 2014). Real-time PCR based methods are the most cost-effective and require shorter working times than other methods.

Using NGS technologies, it is possible to screen simultaneously multiple mutations in multiple genes in a single test run. Detection of targeted oncogene mutations, including KRAS mutations, in CRC formalin-fixed, paraffin-embedded specimens by NGS has been reported to have an accuracy of 96.1% (compared with Sanger sequencing) and 99.6% (compared with real-time PCR methods). Unfortunately, NGS is limited in its sensitivity for detection of low-occurrence (<5%) mutations.

To evaluate the inventive approach for enhancing the sensitivity of NGS detection of KRAS mutations DNA was extracted from FFPE or EDTA whole blood/stool samples. Normal and cancer samples are used. Cancer was confirmed using standard diagnostic procedures including morphologic evaluation, FISH testing, flow cytometry, cytogenetic analysis and immunohistochemistry. It should be noted that other sources of DNA may be used, including, but not limited to, biopsied tissue, bone marrow, fine needle aspirate (FNA), and peripheral blood.

The high sensitivity testing was performed on more than 30 DNA samples with specific mutations as well as on 4 samples without any mutations as a negative control.

DNA extraction: We extracted DNA using the QIAamp DNA Mini Kit (Qiagen; Venlo, Netherlands) in both manual and automated (QIAcube) extractions according to manufacturer's instruction. Extracted DNA was then quantified using a Nanodrop 2000 (Thermo Fisher Scientific; Waltham, Mass., U.S.A.) instrument and adjusted to approximately 50-100 ng/μL with water.

Using known techniques, targeted sequencing is performed to isolated and sequence a subset of genes or regions of the DNA obtained from the samples. Targeted sequencing panels can be purchased with preselected content or custom-designed using procedures known in the art using any of a number of commercially-available targeted sequencing library prep kits according to the manufacturer's instructions.

Procedure for Amplicon-Based NGS:

Referring to FIG. 1B, for amplicon-based NGS 100, one pair of oligos (Probe 1, Probe 2) is designed for each amplicon. In step 120, hybridization of these oligos to unfragmented genomic DNA is performed in a 96 well plate, followed by extension and ligation in step 122 to form a DNA template consisting of the regions of interest flanked by universal primer sequences. Using indexed primers supplied with the kit, DNA templates are then PCR amplified in step 124 and pooled into a single tube. The final amplicon is sequenced on the Illumina MiSeq or NextSeq System in step 126. The sequence data is analysed using available bioinformatics software and output via a user interface 128.

FIG. 1A diagrammatically illustrates the modified procedure for amplicon-based NGS 102 according to the invention in which an LNA blocking oligonucleotide is added during amplification. The LNA oligo is designed so that it anneals to the template strand during the primer annealing step of PCR and melts from mutant template DNA—but not WT DNA—during extension. Because a single nucleotide mismatch in the LNA-DNA hybrid greatly decreases its melting temperature ($T_m$), only mutant template DNA is free to complete its extension. Therefore, WT DNA is amplified linearly but mutant DNA is amplified exponentially.

Using a standard gene panel for detecting mutations in cancer, we demonstrate the ability to increase the sensitivity of detecting KRAS mutation by adding a LNA probe that covers the mutation site. A target-specific cancer panel (TSACP) includes 48 cancer genes with 212 amplicons in a highly multiplexed, single tube reaction. The TSA-Myeloid panel has 54 genes with 581 amplicons in a highly multiplexed, single tube reaction. This highly targeted approach enables a wide range of applications for discovering, validating, and screening genetic variants in a rapid and efficient manner. With the ability to combine hundreds of amplicons per sample and up to 96 samples per run, the TSACP or TSA-Myeloid Panel provide unprecedented level of sample multiplexing, while providing excellent specificity and uniformity. See Table 1 for a listing of TSACP genes and Table 2 for a listing of TSA-Myeloid genes.

TABLE 1

| |
|---|
| ABL1 |
| AKT1 |
| ALK |
| APC |
| ATM |
| BRAF |
| CDH1 |
| CDKN2A |
| CSF1R |
| CTNNB1 |
| EGFR |
| ERBB2 |
| ERBB4 |
| FBXW7 |
| FGFR1 |
| FGFR2 |
| FGFR3 |
| FLT3 |
| GNA11 |
| GNAQ |
| GNAS |
| HNF1A |
| HRAS |
| IDH1 |
| JAK2 |
| JAK3 |
| KDR |
| KIT |
| KRAS |
| MET |
| MLH1 |
| MPL |
| NOTCH1 |
| NPM1 |
| NRAS |
| PDGFRA |
| PIK3CA |
| PTEN |
| PTPN11 |
| RB1 |
| RET |
| SMAD4 |
| SMARCB1 |
| SMO |
| SRC |
| STK11 |
| TP53 |
| VHL |

TABLE 2

| GENE |
|---|
| ABL1 |
| ASXL1 |
| ATRX |
| BCOR |
| BCORL1 |
| BRAF |
| CALR |

TABLE 2-continued

| GENE |
| --- |
| CBL |
| CBLB |
| CBLC |
| CKDN2A |
| CEBPA |
| CSF3R |
| CUX1 |
| DNMT3A |
| ETV6/TEL |
| EZH2 |
| FBXW7 |
| FLT3 |
| GATA1 |
| GATA2 |
| GNAS |
| HRAS |
| IDH1 |
| IDH2 |
| IKZF1 |
| JAK2 |
| JAK3 |
| KDM6A |
| KIT |
| KRAS |
| MLL |
| MPL |
| MYD88 |
| NOTCH1 |
| NPM1 |
| NRAS |
| PDGFRA |
| PFH6 |
| PTEN |
| PTPN11 |
| RAD21 |
| RUNX1 |
| SETBP1 |
| SF3B1 |
| SMC1A |
| SMC3 |
| SRSF2 |
| STAG2 |
| TET2 |
| TP53 |
| U2AF1 |
| WT1 |
| ZRSR2 |

As will be readily apparent to those in the art, larger or smaller gene panels may be used.

Procedure for Hybrid Capture NGS

We used a custom panel designed in Illumina Design Studio. We used 315 cancer relevant genes as an input template. A listing of the genes is provided as FIG. 7.

Other than the TERC gene using exons, all the rest of the genes are using CDS only. Select "Dense" for probe selection. The design summary is as following:

Cumulative target size: 907,395 bp
Final probe: 10367;
Gap: 0;
Coverage: 100%

This assay used the standard NGS Nextera Rapid Capture Custom Enrichment workflow. DNA was extracted from EDTA WB, BM or FFPE using Qiacube instrument and quantified using the Qubit DNA BR assay kit. Nextera enrichment-based sample preparation generates adaptor-tagged libraries from 50 ng input genomic DNA. Nextera tagmentation of DNA simultaneously fragments and tags DNA without the need for mechanical shearing. Integrated sample barcodes allow the pooling of up to 12 adaptor ligated sample libraries into a single, hybridization-based, pull down reaction. The pooled libraries are then denatured into single-stranded DNA and biotin-labeled probes complementary to the targeted region are used for the Rapid Capture hybridization. Streptavidin beads are added, which bind to the biotinylated probes that are hybridized to the targeted regions of interest. Magnetic pull down of the streptavidin beads enriches the targeted regions that are hybridized to biotinylated probes. The enriched DNA fragments are then eluted from the beads and a second round of rapid capture is completed to increase enrichment specificity.

The NDST custom pools sequenced on MiSeq are analyzed using MiSeq reporter (MSR). The enrichment workflow from MSR generates aligned sequence reads in the .bam file format using the BWA algorithm and performs indel realignment using the GATK indel realignment tool. Variant calling occurs in the target regions specified in the manifest file. The GATK variant caller generates .vcf files that contain genotype, annotation and other information across all sites in the specified target region.

Coverage files containing coverage depth in the genome and within gaps are also generated. The enrichment summary statistics contain the on-target and off-target reads/base, average coverage in the target region, % reads that are present at 1X, 10X, 20X and 50X coverage, uniformity of the coverage, all listed in the each samples enrichment sequencing report.

High Sensitivity NGS Testing:

To convert the standard NGS procedures described above to high sensitivity (HS) assays, we add LNA or BNA (Block Nucleic Acid) corresponding to the wild-type DNA to prevent amplification and to selectively sequence mutant DNA. In principle this can be done using any nucleic acid that prevents the amplification of wild-type, which is a necessary step in amplicon-based NGS as well as to a lesser degree in hybrid capture NGS. The oligo LNA is usually around 10mer to 12 mer with a sequence identical to the wild-type DNA corresponding to the hot-spot were the mutation of interest is located. Multiple oligonucleotides identical to wild-types covering multiple loci can used at the same time. We use 4 µM to 40 nM/per sample dependent on the quantity of input DNA. The LNA oligos are designed to feature a 3' inverted dT to inhibit both extension by DNA polymerase and degradation by 3' exonuclease. The BNA oligos are designed with a 3' phosphate for the same reason. In all procedures, LNA or BNA is added to the sample prior to amplification step, as shown in FIG. 1A for amplicon-based NGS.

Figure 2A:
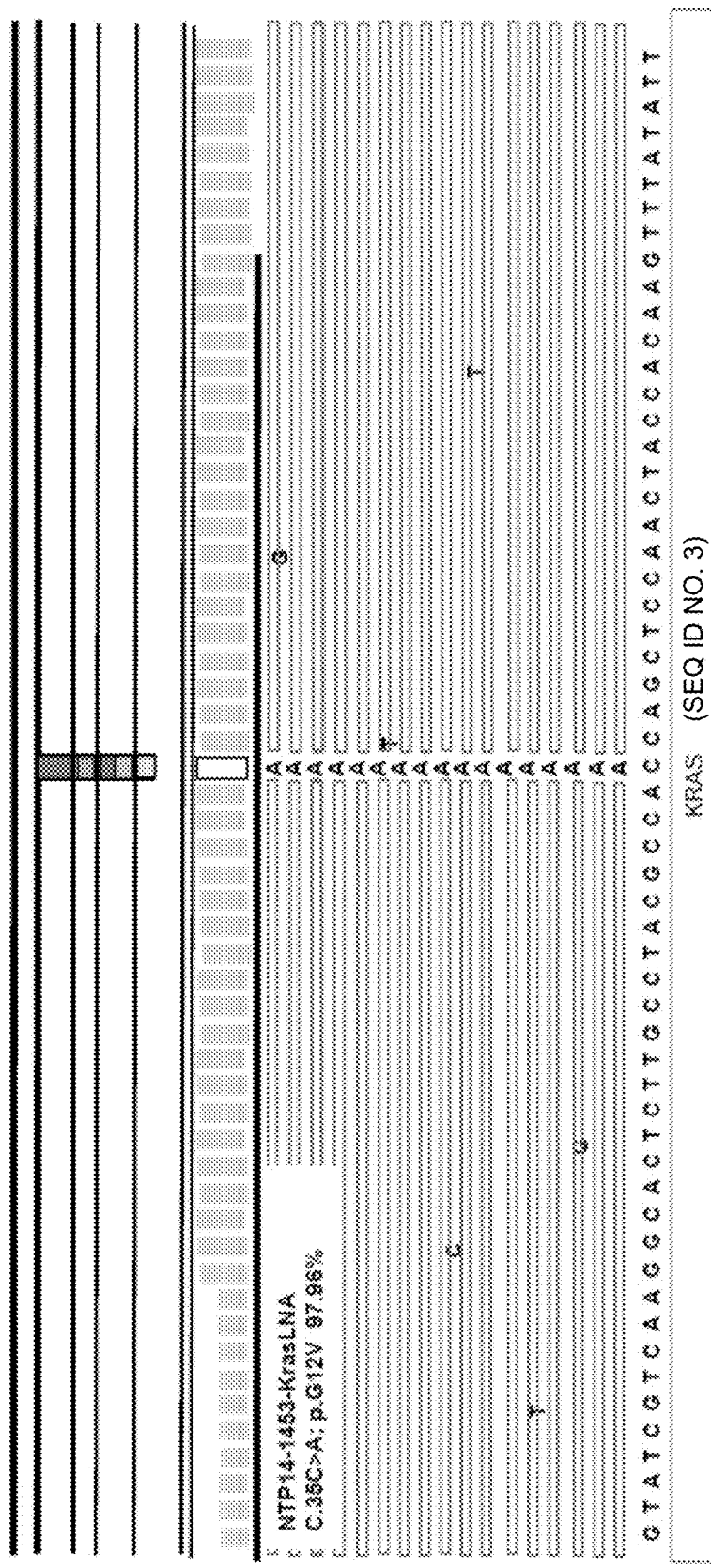
FIGS. 2A and 2B show NGS results showing the mutation (C>A) in KRAS as detected in the same sample using LNA blocking (FIG. 2A) and the mutation without LNA blocking (FIG. 2B).
Figure 2B:
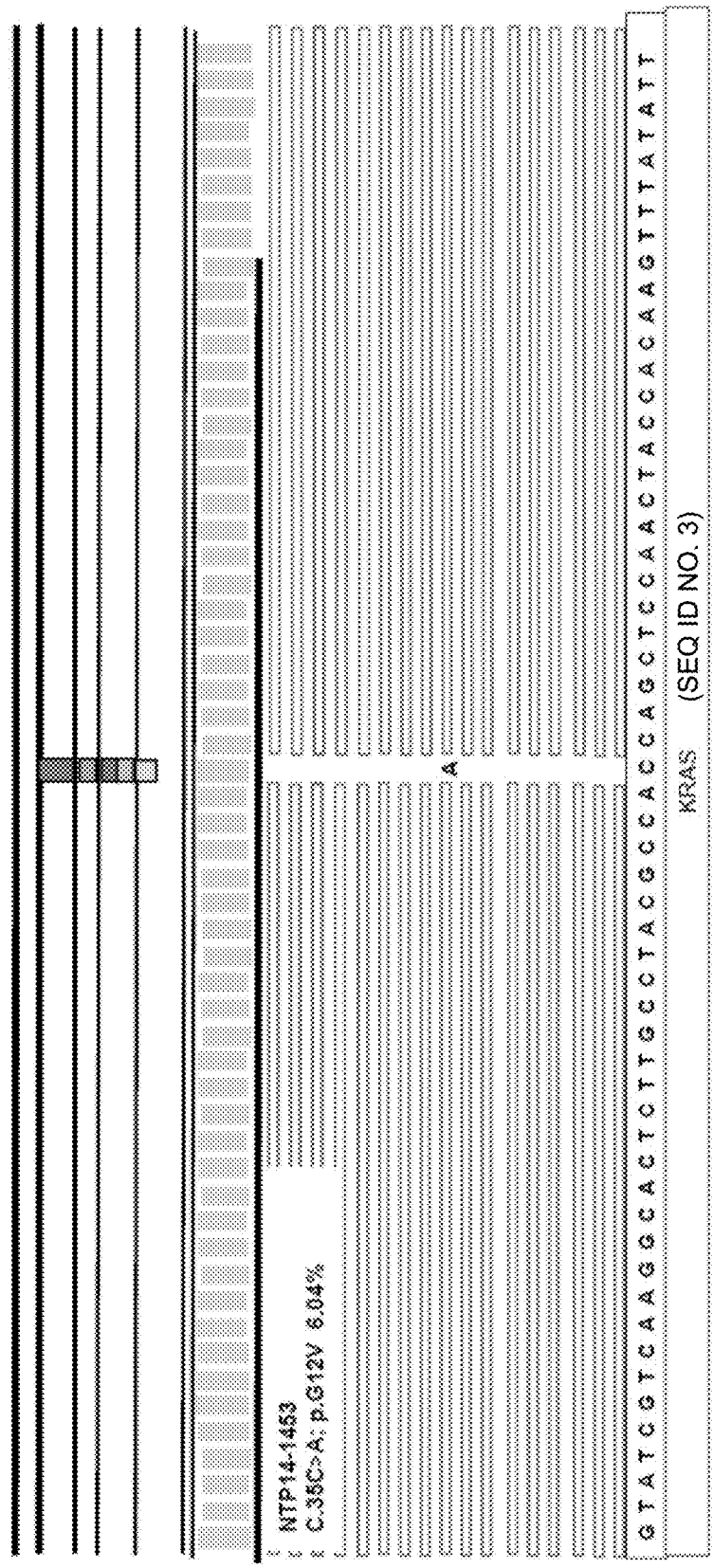

For detection of KRAS mutations, we added a probe spanning codon 12(CCTACGCCACAGCTCCAA) (SEQ ID NO. 1) to the reagents used for this assay prior to amplification. FIG. 2A is a representative image from the Integrative Genome Viewer (IGV) (Broad Institute) with visual confirmation of KRAS mutations detected using LNA blocking, demonstrating a mutation rate of 98%, which can be compared to the 6% rate seen in FIG. 2B. The table shown in FIG. 3 provides a comparison of the results obtained using LNA and without LNA, demonstrating the significant difference (16 fold enrichment) in the percentage of mutant DNA.

EXAMPLE 2

Enhancing Sensitivity of NGS in Detecting EGFR Mutation

Figure 5:
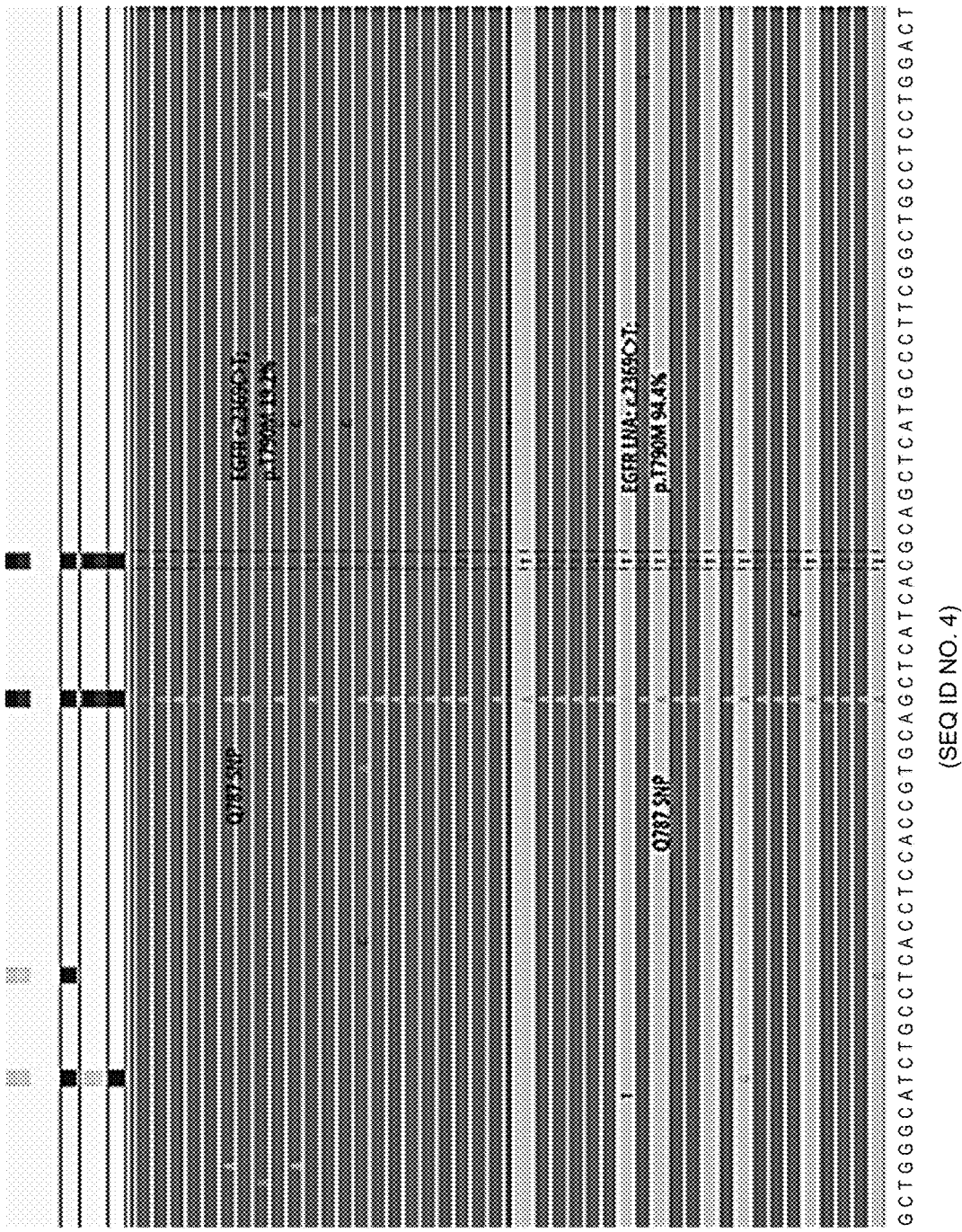
FIG. 5 shows NGS results showing the mutation (C>T) in EGFR T790 as detected in the same sample without LNA (Top panel) and with LNA (Lower panel).

Using a similar gene panel as described above for detecting mutations in cancer, we demonstrate that we can increase the sensitivity of detecting EGFR T790 mutation by adding an LNA probe that covers the mutation site. In this case, we added a probe covering the T790 codon (CTCATCACGCAGCTC) (SEQ ID NO. 2) to the reagents used for this assay at the time of amplification. The table of FIG. 4 provides a comparison of the results obtained using LNA and without LNA, again showing a significant difference in the percentage of mutant DNA. Without LNA, the mutation rate for T790 was 19%, yielding and inconclusive result, i.e., "No selection". After adding the LNA oligo as described prior to amplification, the mutation rate, and hence, the sensitivity, was greatly enhanced, i.e., "Selection", exhibiting a 5-fold increase to 94%, as shown in FIG. 5.

EXAMPLE 3

Enhancing Sensitivity of NGS in Detecting EGFR Mutation

Non-small-cell lung cancer (NSCLC) is one of the most frequent human malignancies, constituting about 80% of all lung tumors. NSCLC can be divided into genetic subsets on the basis of the activating mutations that they harbor; each of these subsets may correspond to patient cohorts that are likely to benefit from treatment with specific inhibitors.

Activating mutations in the epidermal growth factor receptor (EGFR), affecting hotspots within exons that code for the tyrosine kinase domain, can be found in 10-40% of NSCLC patients, mostly in adenocarcinomas. About 50% of mutated patients harbor in-frame deletions in exon 19, (around codons 746 to 750) and 35-45% show the substitution of leucine 858 by an arginine in the exon 21. The remaining mutants are insertions in exon 20 (5%) and uncommon substitutions spanning exons from 18 to 21,such as L861Q. These specific mutations are related to a higher sensitivity to the tyrosine kinase inhibitors (TKIs) erlotinib and gefitinib, whereas the EGFR T790 M mutation in exon 20 is observed in 50% of cases with acquired resistance to erlotinib and gefitinib and has also been detected in 38% of patients with de novo drug resistance.

We also analyzed an additional nine random samples from patients who had previously been tested positive for lung cancer with known EGFR mutations using the LNA blocking approach. The results for testing for EGFR mutation on exons 18, 19, 20 or 21 are provided in FIG. 6. One of the 9 patients (Case No. MOL15-001572) had already been flagged as having a T790 mutation, determined previously by NGS, albeit at a low percentage. As expected, the one patient with T790 mutation exhibited the same mutation after employed LNA blocking, but at significantly a higher percentage. In addition, another of the nine patients (Case No. MOL15-001877) showed a mutation in T790 that had not been previously detected without the enhanced sensitivity provided by the inventive technique of LNA blocking.

Previously-published data suggested that when Sanger sequencing is used for mutation analysis, blocking the wild-type DNA during amplification for Sanger sequencing may increase the sensitivity of the Sanger sequencing and allow the detection of relatively low levels of mutation. This was reported for BRAF V600, KRAS, PIK3CA, and EGFR L858 mutations (references 1-5, listed below). These techniques are in general considered as an alternative to the next generation sequencing (NGS). Because of the different approaches used in NGS and Sanger sequencing, i.e., isolation and individual sequencing of DNA fragments in NGS versus simultaneous sequencing of all molecules in Sanger sequencing, there is no motivation in the prior art to employ blocking probes to NGS.

The inventor believes that the above-described experiments represent the first time that LNA has been used to enrich for mutation for the purpose of NGS sequencing. The inventive approach demonstrates significant improvement of sensitivity of the NGS. While this is applied here to KRAS and EGFR T790 mutation, the same approach can be used for other types of mutations as well as for multiple mutations in multiple genes that are tested together in NGS. In addition, while the examples described herein employ LNA probes as the mechanism for blocking amplification of the wild-type DNA, other blocking materials may be used, including BNA, QClamp and ICE COLD-PCR may be used.

REFERENCES (INCORPORATED HEREIN BY REFERENCE)

1. Komatsu H, Tsunoda T, Inui A, Sogo T, Fujisawa T, Imura M, Tateno A., "Successful use of saliva without DNA extraction for detection of macrolide-resistant Mycoplasma pneumoniae DNA in children using LNA probe-based real-time PCR", *J Infect Chemother.* 2013 Dec;19 (6):1087-92. doi: 10.1007/s10156-013-0630-9. Epub 2013 Jun 17.
2. Ang D, O'Gara R, Schilling A, Beadling C, Warrick A, Troxell M L, Corless C L., "Novel method for PIK3CA mutation analysis: locked nucleic acid-PCR sequencing", *J Mol Diagn.* 2013 May;15(3):312-8. doi: 10.1016/j.jmoldx.2012.12.005. Epub 2013 Mar 27.
3. Dono M, Massucco C, Chiara S, Sonaglio C, Mora M, Truini A, Cerruti G, Zoppoli G, Ballestrero A, Truini M, Ferrarini M, Zupo S., "Low percentage of KRAS mutations revealed by locked nucleic acid polymerase chain reaction: implications for treatment of metastatic colorectal cancer", *Mol Med.* 2013 Feb 8;18:1519-26. doi: 10.2119/molmed.2012.00175.
4. Skronski M, Chorostowska-Wynimko J, Szczepulska E, Szpechcinski A, Rudzinski P, Orlowski T, Langfort R., "Reliable detection of rare mutations in EGFR gene codon L858 by PNA-LNA PCR clamp in non-small cell lung cancer", *Adv Exp Med Biol.* 2013;756:321-31. doi: 10.1007/978-94-007-4549-0_39.
5. Morandi L, de Biase D, Visani M, Cesari V, De Maglio G, Pizzolitto S, Pession A, Tallini G., "Allele specific locked nucleic acid quantitative PCR (ASLNAqPCR): an accurate and cost-effective assay to diagnose and quantify KRAS and BRAF mutation", *PLoS One.* 2012;7(4): e36084. doi: 10.1371/journal.pone.0036084. Epub 2012 Apr 30.

The invention claimed is:

1. A method of detecting a low-occurrence mutation in a sample from a patient, the method comprising:
   isolating DNA from the sample;
   adding a blocking probe to the isolated DNA, the blocking probe comprising an oligonucleotide complementary to wild-type DNA corresponding to the sample, the blocking probe adapted to span a site of a suspected mutation within a region of interest in the isolated DNA, wherein the region of interest is KRAS codon 12 and the blocking probe is CCTACGCCACAGCTCCAA (SEQ ID NO. 1);
   amplifying the isolated DNA;
   sequencing fragments of the amplified DNA in parallel; and
   generating an output corresponding to the sequenced fragments.

2. The method of claim 1, wherein the blocking probe is locked nucleic acid (LNA).

3. The method of claim 1, further comprising, prior to adding a blocking probe, fragmenting the isolated DNA into fragments comprising one or more regions of interest.

4. The method of claim 1, further comprising, prior to amplifying the isolated DNA, fragmenting and tagging the isolated DNA with one or more enrichment probes.

5. The method of claim 1, wherein the sample is selected from the group consisting of whole blood, stool, biopsied tissue, bone marrow, fine needle aspirate (FNA), and peripheral blood.

6. A method for detecting a low-occurrence mutation in isolated DNA comprising:
   adding a blocking probe to reagents during amplification of the isolated DNA, wherein the blocking probe comprises an oligonucleotide complementary to wild-type DNA corresponding to the sample, the blocking probe adapted to span a site of a suspected mutation within a region of interest in the isolated DNA, wherein the region of interest is KRAS codon 12 and the blocking probe is CCTACGCCACAGCTCCAA (SEQ ID NO. 1);
   sequencing fragments of the amplified DNA in parallel; and
   generating an output corresponding to the sequenced fragments.

7. The method of claim 6, wherein the blocking probe is locked nucleic acid (LNA).

8. The method of claim 6, further comprising, prior to adding a blocking probe, fragmenting the isolated DNA into fragment comprising one or more regions of interest.

9. The method of claim 6, further comprising, prior to amplifying the isolated DNA, fragmenting and tagging the isolated DNA with one or more enrichment probes.

10. The method of claim 6, wherein the sample is selected from the group consisting of whole blood, stool, biopsied tissue, bone marrow, fine needle aspirate (FNA), and peripheral blood.

\* \* \* \* \*

SEQUENCE LISTING

<160> NUMBER OF SEQ ID NOS: 5

<210> SEQ ID NO 1
<211> LENGTH: 18
<212> TYPE: DNA

```
<213> ORGANISM: Artificial Sequence
<220> FEATURE:
<223> OTHER INFORMATION: Synthetic oligonucleotide

<400> SEQUENCE: 1
cctacgccac agctccaa                                                 18

<210> SEQ ID NO 2
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 2
ctcatcacgc agctc                                                    15

<210> SEQ ID NO 3
<211> LENGTH: 57
<212> TYPE: DNA
<213> ORGANISM: Homo sapiens

<400> SEQUENCE: 3
gtatcgtcaa ggcactcttg cctacgccac cagctccaac taccacaagt ttatatt      57

<210> SEQ ID NO 4
<211> LENGTH: 71
<212> TYPE: DNA
<213> ORGANISM: Homo sapiens

<400> SEQUENCE: 4
gctgggcatc tgcctcacct ccaccgtgca gctcatcacg cagctcatgc ccttcggctg   60
cctcctggac t                                                        71

<210> SEQ ID NO 5
<211> LENGTH: 15
<212> TYPE: DNA
<213> ORGANISM: Homo sapiens

<400> SEQUENCE: 5
ggaattaaga gaagc                                                    15
```